United States Patent
Keer et al.

(10) Patent No.: US 11,660,310 B2
(45) Date of Patent: May 30, 2023

(54) LOW DOSE COMBINATION CDA SUBSTRATE DRUG/CEDAZURIDINE WITH EXTENDED ADMINISTRATION

(71) Applicant: Otsuka Pharmaceutical Co., Ltd., Tokyo (JP)

(72) Inventors: Harold Keer, Pleasanton, CA (US); Mohammad Azab, Pleasanton, CA (US); Aram Oganesian, Dublin, CA (US)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 17/560,485

(22) Filed: Dec. 23, 2021

(65) Prior Publication Data
US 2022/0110958 A1  Apr. 14, 2022

Related U.S. Application Data

(62) Division of application No. 16/574,924, filed on Sep. 18, 2019, now Pat. No. 11,224,610.

(60) Provisional application No. 62/733,277, filed on Sep. 19, 2018.

(51) Int. Cl.
 *A61K 31/706* (2006.01)
(52) U.S. Cl.
 CPC .................. *A61K 31/706* (2013.01)
(58) Field of Classification Search
 CPC .............. A61K 31/713; A61K 31/7068; A61K 31/706
 See application file for complete search history.

(56) References Cited

U.S. PATENT DOCUMENTS

| | | |
|---|---|---|
| 8,268,800 B2 * | 9/2012 | Hamilton ........... A61K 31/7068 536/28.4 |
| 8,329,666 B2 | 12/2012 | Belyakov et al. |
| 9,259,469 B2 | 2/2016 | Desimone et al. |
| 9,834,576 B2 | 12/2017 | Choi et al. |

OTHER PUBLICATIONS

"Clinicaltrials.gov NCT02103478 Pharmacokinetic Guided; Dose Escalation and Dose Confirmation with Oral Decitabine and Oral CDAi in Patients with MDS (Apr. 2014)".
"Clinicaltrials.gov NCT03502668 Phase 1-2 study of Low Dose ASTX727 (ASTX272LD) in Lower Risk MDS (Apr. 2018)".
"Steensma, D. "Extended Abstract: Treatment of Lower-Risk Myelodysplastic Syndromes", Clinical Lymphoma Myeloma & Leukemia 18:817-818 (2018)".
Ball, et al., ""Hypomethylating agent combination strategies in myelodysplastic syndromes: Hopes and shortcomings", Leuk Lymphoma 58(5):1022-1036 (May 2017)".
Desimone, et al., ""Tetrahydrouridine, cytidine analogues, and hemoglobin F", Am. J. Hematology 18(3):283-288 (1985)".
Ebrahem, et al., ""High cytidine deaminase expression in the liver provides sanctuary far cancer cells from decitabine treatment effects", On otarget 3(10):1137-1145 (Sep. 27, 2012)".
Garcia-Manero, et al., ""Randomized Open-Label Phase II Study of Decitabine in Patients with Low- or Intermediate-Risk Myelodysplastic Syndromes", J Clinical Oncology (31)20:2548-2553 (Jul. 10, 2013)".
Garcia-Manero, et al., ""Successful Emulation of IV Decitabine Pharmacokinetics with an Oral Fixed-Dose Combination of the Oral Cytidine Deaminase Inhibitor (CDAi) E7727 with Oral Decitabine, in Subjects with Myelodysplastic Syndromes (MDS): Final Data of Phase 1 Study", Blood; 128(22):114 (Dec. 2, 2016)".
Gowher, et al., ""Mechanism of inhibition of DNA methyltransferases by cytidine analogs in cancer therapy", Cancer Biology & Therapy 3(11):1062-1068 (Oct. 15, 2004)".
Jabbour, et al., ""Randomized phase 2 study of low-dose decitabine vs low-dose azacitidine in lower-risk MDS and MDS/MPN", Blood 130(13):1514-1522 (Sep. 28, 2017)".
Kantarjian, et al., ""Results of a randomized study of 3 schedules of low-dose decitabine in higher-risk myelodysplastic syndrome and chronic myelomonocytic leukemia". Blood 109(1):52-57 (Jan. 2007)".
Lee, et al., ""Benefits of hypomethylating therapy in IPSS lower-risk myelodysplastic syndrome patients: A retrospective multicenter case series study", Leukemia Research 60:135-144 (Aug. 15, 2017)".
Lemaire, et al., ", "Enhancement of antineoplastic action of aza-'-deoxycytidine by zebularine on L1210 leukemia," Anticancer Drugs 16:301-308 (2005)".
Mahfouz, et al., ""Increased CDA Expression/Activity in Males Contributes to Decreased Cytidine Analog Half-Life and Likely Contributes to Worse Outcomes with 5-Azacytidine or Decitabine Therapy", Clin Cancer Res. 19(4):938-948 (Jan. 3, 2013)".
Nikitich et al. "Evaluation of Potential Low-Dose Regimens of Oral Fixed-Dose Combination of Cytidine Deaminase Inhibitor E7727 with Decitabine (ASTXT27-LD) to Minimize Decitabine-Mediated Neutropenia in Low-Risk MDS Subjects Using Systems Pharmacology Modeling" ACoP8, Fort Lauderdale, FL, Oct. 15-18, 2017, posted online Sep. 2017.
Saunthararajah, et al., ""Evaluation of noncytotoxic DNMT1-depleting therapy in patients with myelodysplastic syndromes", JCI 125(3):1043-1055 (Mar. 2015)".
Ueda, et al., ""Low-Dose Azacitidine with DNMT1 Level Monitoring to Treat Post-Transplantation Acute Myelogenous Leukemia or Myelodysplastic Syndrome Relapse", Biol Blood Marrow Transplant 000:1-6 (2019)".
Uy, et al., ""Hypomethylating Agents (HMA) Treatment for Myelodysplastic Syndromes: Alternatives in the Frontline and Relapse Settings", Expert Opin Pharmacother. 18(12);1213-1224 (Aug. 2017)".

* cited by examiner

*Primary Examiner* — Pancham Bakshi
(74) *Attorney, Agent, or Firm* — Myers Bigel, P.A.

(57) ABSTRACT

This invention relates to methods and compositions for administering an effective amount of a CDA substrate drug and an effective amount of cedazuridine. In particular, the invention relates to methods for treating cancer, inhibiting degradation of a CDA substrate drug, and reducing DNA methylation in a subject in need thereof comprising administering an effective amount of a CDA substrate drug and an effective amount of cedazuridine.

19 Claims, 6 Drawing Sheets

LOW DOSE COMBINATION CDA SUBSTRATE DRUG/CEDAZURIDINE WITH EXTENDED ADMINISTRATION

STATEMENT OF PRIORITY

This application is a divisional of and claims priority to U.S. patent application Ser. No. 16/574,924, filed on Sep. 18, 2019, which claims the benefit, under 35 U.S.C. § 119(e), of U.S. Provisional Application No. 62/733,277, filed on Sep. 19, 2018, the entire contents of each of which are incorporated by reference herein.

FIELD OF THE INVENTION

This invention relates to methods and compositions for administering an effective amount of a CDA substrate drug and an effective amount of cedazuridine. In particular, the invention relates to methods for treating cancer, inhibiting degradation of a CDA substrate drug, and reducing DNA methylation in a subject in need thereof comprising administering an effective amount of a CDA substrate drug and an effective amount of cedazuridine.

BACKGROUND OF THE INVENTION

The enzymes adenosine deaminase (ADA, EC 3.5.4.4) and cytidine deaminase (CDA, EC 3.5.4.5) function to deaminate natural aminopurine and aminopyrimidine nucleosides, respectively, in human and other organisms. They may also convert active nucleoside-based drugs into inactive metabolites. For example, the purine nucleoside drug arabinosyladenine (fludarabine, ara-A) is deaminated by ADA; the resulting compound, with the parent amino group replaced with hydroxyl, is inactive as an antitumor agent compared to the parent compound. Similarly, the antileukemia drug arabinosylcytosine (cytarabine, also known as ara-C) is metabolically degraded by CDA into inactive arabinosyluracil.

CDA is a component of the pyrimidine salvage pathway. It converts cytidine and deoxycytidine to uridine and deoxyuridine, respectively, by hydrolytic deamination (*Arch. Biochem. Biophys.* 1991, 290, 285-292; *Methods Enzymol.* 1978, 51, 401-407; *Biochem. J.* 1967, 104, 7P). It also deaminates a number of synthetic cytosine analogs which are clinically useful drugs, such as ara-C (*Cancer Chemother. Pharmacol.* 1998, 42, 373-378; *Cancer Res.* 1989, 49, 3015-3019; *Antiviral Chem. Chemother.* 1990, 1, 255-262). Conversion of the cytosine compounds to the uridine derivatives usually confers loss of therapeutic activity or addition of side-effects. It has also been shown that cancers that acquire resistance to cytosine analog drugs often overexpress CDA (*Leuk. Res.* 1990, 14, 751-754). Leukemic cells expressing a high level of CDA can manifest resistance to cytosine antimetabolites and thereby limit the antineoplastic activity of such therapeutics (*Biochem. Pharmacol.* 1993, 45, 1857-1861).

The present invention overcomes shortcomings in the art by providing methods for treating cancer, inhibiting degradation of a CDA substrate drug, and/or reducing DNA methylation in a subject in need thereof comprising administering an effective amount of a CDA substrate drug and an effective amount of cedazuridine.

SUMMARY OF THE INVENTION

The present invention is based, in part, on the development of low dose (LD) administration schedules of combination decitabine/cedazuridine that result in improved epigenetic effects and decreased myelosuppressive effects in cancer patients.

Thus, one aspect of the invention relates to methods for treating cancer in a subject in need thereof, comprising administering to the subject: (i) an effective amount of a CDA substrate drug (e.g., decitabine); and (ii) an effective amount of cedazuridine, thereby treating cancer in the subject.

An additional aspect of the invention relates to methods for inhibiting degradation of a CDA substrate drug (e.g., decitabine, e.g., 5-azacytidine) in a subject in need thereof, comprising administering to the subject: (i) an effective amount of a CDA substrate drug (e.g., decitabine, e.g., 5-azacytidine); and (ii) an effective amount of cedazuridine, thereby inhibiting degradation of the CDA substrate drug in the subject.

A further aspect of the invention relates to methods of reducing DNA methylation (e.g., LINE-1 methylation) in a subject in need thereof, comprising administering to the subject: (i) an effective amount of a CDA substrate drug; and (ii) an effective amount of cedazuridine, thereby reducing DNA methylation in the subject.

These and other aspects of the invention are set forth in more detail in the description of the invention below.

DETAILED DESCRIPTION OF THE INVENTION

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, nucleotide sequences, amino acid sequences and other references mentioned herein are incorporated by reference in their entirety.

Definitions

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

As used herein, the transitional phrase "consisting essentially of" is to be interpreted as encompassing the recited materials or steps and those that do not materially affect the basic and novel characteristic(s) of the claimed invention. Thus, the term "consisting essentially of" as used herein should not be interpreted as equivalent to "comprising."

"Effective amount" refers to the amount required to produce a desired effect (e.g., enhancing the half-life, bioavailability or efficacy of a CDA substrate drug, treating cancer in a subject, reducing DNA methylation in a subject, inhibiting cytidine deaminase in a subject, or inhibiting degradation of a CDA substrate drug by cytidine deaminase).

"Half-life" refers to the period of time required for the concentration or amount of a compound in a subject to be reduced to exactly one-half of a given concentration or amount.

"Pharmaceutically acceptable" refers to those properties and/or substances that are acceptable to the patient from a pharmacological and/or toxicological point of view, and/or to the manufacturing pharmaceutical chemist from a physical and/or chemical point of view regarding composition, formulation, stability, patient acceptance, bioavailability and compatibility with other ingredients.

"Pharmaceutically acceptable excipient" can mean any substance, not itself a therapeutic agent, used as a carrier, diluent, adjuvant, binder, and/or vehicle for delivery of a therapeutic agent to a subject, or added to a pharmaceutical composition to improve its handling or storage properties or to permit or facilitate formation of a compound or composition into a unit dosage form for administration. Pharmaceutically acceptable excipients are well known in the pharmaceutical arts and are described, for example, in Remington's Pharmaceutical Sciences, Mack Publishing Co., Easton, Pa. (e.g., 20th Ed., 2000), and Handbook of Pharmaceutical Excipients, American Pharmaceutical Association, Washington, D.C., (e.g., 1st, 2nd and 3rd Eds., 1986, 1994 and 2000, respectively). As will be known to those skilled in the art, excipients may provide a variety of functions and may be described as wetting agents, buffering agents, suspending agents, lubricating agents, emulsifiers, disintegrants, absorbents, preservatives, surfactants, colorants, flavorants, and sweeteners. Examples of pharmaceutically acceptable excipients include without limitation: (1) sugars, such as lactose, glucose and sucrose; (2) starches, such as corn starch and potato starch; (3) cellulose and its derivatives, such as sodium carboxymethyl cellulose, ethyl cellulose, cellulose acetate, hydroxypropylmethylcellulose, and hydroxypropylcellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

"Pharmaceutically acceptable salt" refers to an acid or base salt of a compound of the invention, which salt possesses the desired pharmacological activity and is neither biologically nor otherwise undesirable. The salt can be formed with acids that include without limitation acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate and undecanoate. Examples of a base salt include without limitation ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. In some embodiments, the basic nitrogen-containing groups can be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as phenethyl bromides.

"Unit dosage form" refers to a physically discrete unit suitable as a unitary dosage for human or other animal subjects. Each unit dosage form may contain a predetermined amount of an active substance (e.g., compound or composition of the invention, CDA substrate drug and/or other therapeutic agent) calculated to produce a desired effect.

"Optional" or "optionally" means that the subsequently described event or circumstance may or may not occur, and that the description includes instances where the event or circumstance occurs and instances in which it does not. For example, an alkyl that is "optionally substituted" encompasses both an alkyl that is unsubstituted and an alkyl that is substituted.

The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, fifteen-fold, etc.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectible activity (at most, an insignificant amount, e.g., less than about 10% or even 5%).

"Subject" refers to a cell or tissue, in vitro or in vivo, an animal or a human. An animal or human subject may also be referred to as a "patient."

"Animal" refers to a living organism having sensation and the power of voluntary movement, and which requires for its existence oxygen and organic food.

"Mammal" refers to a warm-blooded vertebrate animal with hair or fur. Examples include without limitation members of the human, equine, porcine, bovine, murine, canine or feline species.

By the term "treat," "treating," or "treatment of" (or grammatically equivalent terms) it is meant that the severity of the subject's condition is reduced or at least partially improved or ameliorated and/or that some alleviation, mitigation or decrease in at least one clinical symptom is achieved. "Treating" in reference to a disease, disorder or condition may refer to: (i) inhibiting a disease, disorder or condition, e.g., arresting its development; and/or (ii) relieving a disease, disorder or condition, e.g., causing regression of the clinical symptoms.

"Preventing" in reference to a disease, disorder or condition refers to preventing a disease, disorder or condition, e.g., causing the clinical symptoms of the disease, disorder or condition not to develop. As used herein, the term "prevent," "prevents," or "prevention" (and grammatical equivalents thereof) may also refer to a delay in the onset of a disease or disorder or the lessening of symptoms upon onset of the disease or disorder. The terms are not meant to imply complete abolition of disease and encompass any type of prophylactic treatment that reduces the incidence of the condition or delays the onset and/or progression of the condition.

The term "administering" or "administration" of a compound and/or composition of the present invention to a subject includes any route of introducing or delivering to a subject a compound to perform its intended function. Administration can be carried out by any suitable route, including orally, intranasally, parenterally (intravenously, intramuscularly, intraperitoneally, intracisternally, intrathecally, intraventricularly, or subcutaneously), or topically. Administration includes self-administration and the administration by another.

"Cancer" refers to an abnormal growth of cells which tend to proliferate in an uncontrolled way and, in some cases, to metastasize (spread). Specific cancers types include without limitation the cancers identified in Publication No. U.S. 2006/0014949 and the following: cardiac: sarcoma (e.g., such as angiosarcoma, fibrosarcoma, rhabdomyosarcoma, liposarcoma and the like), myxoma, rhabdomyoma, fibroma, lipoma and teratomas; lung: bronchogenic carcinoma (e.g., such as squamous cell, undifferentiated small cell, undifferentiated large cell, adenocarcinoma and the like), alveolar (e.g., such as bronchiolar) carcinoma, bronchial adenoma, sarcoma, lymphoma, chondromatous hamartoma, mesothelioma; gastrointestinal: esophagus (e.g., such as squamous cell carcinoma, adenocarcinoma, leiomyosarcoma, lymphoma and the like), stomach (e.g., such as carcinoma, lymphoma, leiomyosarcoma and the like), pancreas (e.g., such as ductal adenocarcinoma, insulinoma, glucagonoma, gastrinoma, carcinoid tumors, vipoma and the like), small bowel (e.g., such as adenocarcinoma, lymphoma, carcinoid tumors, Karposi's sarcoma, leiomyoma, hemangioma, lipoma, neurofibroma, fibroma, and the like), large bowel (e.g., such as adenocarcinoma, tubular adenoma, villous adenoma, hamartoma, leiomyoma and the like); genitourinary tract: kidney (e.g., such as adenocarcinoma, Wilm's tumor nephroblastoma, lymphoma, leukemia, and the like), bladder and urethra (e.g., such as squamous cell carcinoma, transitional cell carcinoma, adenocarcinoma and the like), prostate (e.g., such as adenocarcinoma, sarcoma), testis (e.g., such as seminoma, teratoma, embryonal carcinoma, teratocarcinoma, choriocarcinoma, sarcoma, interstitial cell carcinoma, fibroma, fibroadenoma, adenomatoid tumors, lipoma and the like); liver: hepatoma (e.g., hepatocellular carcinoma and the like), cholangiocarcinoma, hepatoblastoma, angiosarcoma, hepatocellular adenoma, hemangioma; bone: osteogenic sarcoma (e.g., such as osteosarcoma and the like), fibrosarcoma, malignant fibrous histiocytoma, chondrosarcoma, Ewing's sarcoma, malignant lymphoma (e.g., such as reticulum cell sarcoma), multiple myeloma, malignant giant cell tumor chordoma, osteochronfroma (e.g., such as osseocartilaginous exostoses), benign chondroma, chondroblastoma, chondromyxofibroma, osteoid osteoma and giant cell tumors; nervous system: skull (e.g., such as osteoma, hemangioma, granuloma, xanthoma, osteitis deformans and the like), meninges (e.g., such as meningioma, meningiosarcoma, gliomatosis and the like), brain (e.g., such as astrocytoma, medulloblastoma, glioma, ependymoma, germinoma [pinealoma], glioblastoma multiform, oligodendroglioma, schwannoma, retinoblastoma, congenital tumors and the like), spinal cord (e.g., such as neurofibroma, meningioma, glioma, sarcoma and the like); gynecological: uterus (e.g., such as endometrial carcinoma and the like), cervix (e.g., such as cervical carcinoma, pre-tumor cervical dysplasia and the like), ovaries (e.g., such as ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma, and the like), vulva (e.g., such as squamous cell carcinoma, intraepithelial carcinoma, adenocarcinoma, fibrosarcoma, melanoma and the like), vagina (e.g., such as clear cell carcinoma, squamous cell carcinoma, botryoid sarcoma (embryonal rhabdomyosarcoma], fallopian tubes (carcinoma) and the like); hematologic: blood (e.g., such as myeloid leukemia [acute and chronic], acute lymphoblastic leukemia, chronic lymphocytic leukemia, myeloproliferative diseases, multiple myeloma, myelodysplastic syndrome and the like), Hodgkin's disease, non-Hodgkin's lymphoma; skin: malignant melanoma, basal cell carcinoma, squamous cell carcinoma, Karposi's sarcoma, moles dysplastic nevi, lipoma, angioma, dermatofibroma, keloids, psoriasis and the like; and adrenal glands: neuroblastoma.

Methods

The present invention is based, in part, on the development of low dose (LD) administration schedules of combination CDA substrate drugs/cedazuridine that result in improved epigenetic effects and decreased myelosuppressive effects in cancer patients. "Low dose" as used herein refers to lower cumulative dose amount per cycle of treatment of a CDA substrate drug (e.g., decitabine, e.g., 5-azacytidine) and/or cedazuridine that are lower than the standard approved dose amounts for these compounds (e.g., when administered alone), either through reduced per-dose amounts and or through modified schedules (e.g., number of days of administering per treatment cycle; e.g., spacing of days of administering per treatment cycle). While not wishing to be bound to theory, the inventors of the present invention have found that low dose administration schedules of decitabine and cedazuridine may provide equivalent or improved epigenetic effects (e.g., LINE-1 demethylation, e.g., % F cell expansion) and/or decreased myelosuppressive effects (e.g., neutropenia) in IPSS-low and IPSS-intermediate-1 MDS cancer patients.

Thus, the present invention provides methods of administering (i) an effective amount of a CDA substrate drug, and (ii) an effective amount of cedazuridine.

As used herein, the term "CDA substrate drug" refers to a drug that can be deaminated by the enzyme cytidine deaminase (CDA). Nonlimiting examples of a CDA substrate include cytidine analogs, such as decitabine, 5-azacytidine, gemcitabine, ara-C (also known as cytarabine), troxacitabine, tezacitabine, 5'-fluoro-2'-deoxycytidine, and cytochlor.

Thus, in some embodiments, the present invention provides a method for treating cancer in subject in need thereof, comprising administering to the subject: (i) an effective amount of a CDA substrate drug; and (ii) an effective amount of cedazuridine, thereby treating cancer in the subject.

Cedazuridine ((4R)-2'-deoxy-2',2'-difluoro-3,4,5,6-tetrahydrouridine; also known as E7727) is a recently developed CDA inhibitor. Cedazuridine in combination with decitabine is in development as a single oral composition referred to as ASTX727. Cedazuridine and methods of making and/or using thereof are further disclosed in U.S. Pat. No. 8,268, 800, the contents of which are incorporated by reference herein in their entirety.

Scheme 1 Structures of three exemplary CDA substrate drugs 5-azacytidine 5-aza-2'-deoxycytidine (decitabine)

ara-C

Scheme 2 Structure of cedazuridine (E7727), CAS No. 1141397-80-9

The CDA substrate drug of the present invention may be any drug that can be deaminated by CDA. In some embodiments, the CDA substrate drug may be 5-azacytidine. In some embodiments, the CDA substrate drug may be decitabine.

Decitabine (5-aza-2'-deoxycytidine) is an antineoplastic agent and hypomethylating agent (HMA) for the treatment of myelodysplastic syndrome (MDS), with potential utility for the treatment of AML and CML as well. Like other cytidine-based drugs, its oral bioavailability and efficacy are limited by deactivation by CDA. Tetrahydrouridine (THU), an inhibitor of CDA, has been shown to improve the potency of decitabine in a sickle cell disease model in baboons (Am. J. Hematol. 1985, 18, 283-288). In addition, another known CDA inhibitor, zebularine, has been shown to enhance the efficacy of decitabine in mice with L1210 leukemia (Anti-cancer Drugs 2005, 16, 301-308).

The cancer treated by the methods of the invention may be any cancer against which the CDA substrate drug is known or later discovered to be effective. In some embodiments, the cancer is selected from hematological cancers and solid cancers. The hematological cancer may be, for example, MDS, leukemia (e.g., ALL, AML, CML, or CMML), or lymphoma (e.g. Hodgkin's Lymphoma, Non-hodgkin lymphoma, or T-cell lymphoma). Examples of solid cancers include, but are not limited to, pancreatic cancer, ovarian cancer, peritoneal cancer, non small cell lung cancer, breast cancer, neuroectodermal tumors, and sarcomas.

In some embodiments, the present invention provides a method for treating cancer, wherein the cancer is MDS. MDS is a group of cancer disorders with shared improper maturation of bone marrow derived blood cells, and symptoms can vary. The International Prognostic Scoring System (IPSS) scores MDS severity into several risk groups based on patient hemoglobin levels, absolute neutrophil count (ANC), platelet count, and percent bone marrow blasts. Risk groups include "low", "intermediate-1", "intermediate-2", and "high". Other risk group scoring methodologies exist such as the Revised IPSS (IPSS-R) and the WHO classification-based Prognostic Scoring System (WPSS), as described in the NCCN Guidelines for Patients, Myelodysplastic Syndromes, 2018. Methods of the present invention may be used to treat cancer in a subject (e.g., a human patient) diagnosed with any risk group of MDS based on any scoring methodology. In some embodiments, a subject in need of the present invention may include a subject diagnosed with lower risk MDS (e.g., IPSS low and/or intermediate-1).

In some embodiments, the present invention provides a method for inhibiting degradation of a CDA substrate drug (e.g., decitabine, e.g., 5-azacytidine) in a subject in need thereof, comprising administering to the subject: (i) an effective amount of a CDA substrate drug; and (ii) an effective amount of cedazuridine, thereby inhibiting degradation of the CDA substrate drug in the subject.

In some embodiments, the present invention provides a method of reducing DNA methylation in a subject in need thereof, comprising administering to the subject: (i) an effective amount of a CDA substrate drug; and (ii) an effective amount of cedazuridine, thereby reducing DNA methylation in the subject (e.g., thereby enabling reduction in DNA methylation by the CDA substrate drug). In some embodiments, the administering reduces DNA methylation of LINE-1. LINE-1 is a long interspersed nuclear element found in human DNA (e.g., the subject) known in the art, and its methylation levels can be measured using standard techniques in the art to determine genetic effects of hypomethylating agents such as CDA substrate drugs (e.g., decitabine).

The administering to a subject in need thereof of (i) an effective mount of a CDA substrate drug, and (ii) an effective amount of cedazuridine has been shown by the inventors of the present invention to provide multiple beneficial responses to the subject. For example, in some embodiments, the administering reduces DNA methylation in the subject by at least 5% (e.g., at least 5, 6, 7, 8, 9, 10, 11, 12, 13, 14, or 15% or more or any value or range therein) as compared to a control measurement, e.g., as compared to DNA methylation in the subject prior to the administering (e.g., subject "baseline" DNA methylation). DNA methylation in the subject may be quantitatively and/or qualitatively evaluated by any standard technique in the art, e.g., as measured by a marker of relative global methylation as compared to a control, e.g., as measured by LINE-1 methylation as compared to a control. For example, in some embodiments, the administering reduces LINE-1 methylation in the subject by at least 5% (e.g., at least 5, 6, 7, 8, 9, 10, 11, 12, 13, 14, or 15% or more) as compared to a control measurement, e.g., as compared to LINE-1 methylation in the subject prior to the administering (e.g., e.g., subject baseline LINE-1 methylation). For example, in some embodiments, the administering may reduce LINE-1 methylation in the subject by at least 5%, at least 8%, at least 10% or at least 15% or more. In some embodiments, the administering may reduce LINE-1 methylation in the subject by about 5% to about 20%, about 6% to about 15%, or by about 8% to about 10%.

In some embodiments, the administering may reduce absolute neutrophil count (ANC) in the subject to less than $0.5 \times 10^9$ cells/L of blood for no more than two weeks (e.g., no more than 14, 13, 12, 11, 10, 9, 8, 7, 6, 5, 4, 3, 2, or 1 consecutive days or any value or range therein) following a 28-day cycle. In some embodiments, the administering reduces absolute neutrophil count (ANC) in the subject to less than $0.5 \times 10^9$ cells/L of blood for no more than two weeks (e.g., more than two, three, four, five, six weeks etc.) during treatment (e.g., between multiple, repeated 28-day cycles).

In some embodiments, a time period of 0 to 31 days or more (e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more) may pass between multiple 28-day treatment cycles of the present invention. The time period of no treatment may be desirable to allow a subject (e.g., a human patient) of the present invention to have adequate health to continue treatment. The time period between treatment cycles can be determined by a physician using standard techniques in the art and may be determined individually on a per-subject basis, for example, as based on adequate blood count, e.g., adequate lack of neutropenia (e.g., absolute neutrophil count (ANC) in the subject of at least or greater than $0.5 \times 10^9$ cells/L), and may be adjusted over the course of treatment based on the judgement of the administering physician. In some embodiments, the time period between treatment cycles may be minimal, e.g., no time period, e.g., immediately starting on the next 28-day time period. In some embodiments, the time period between treatment cycles may be 1 week, 2 weeks, 3 weeks, 4 weeks, 5 weeks, 6 weeks, or more.

In some embodiments, the administering expands hemoglobin F-expressing cells (i.e., F cells) by at least 5% (e.g., at least 5, 6, 7, 8, 9, 10, 15, 20, 25, or 30% or more), optionally as measured by % F cells/erythrocytes per sample (e.g., in a patient blood sample) as compared to a "baseline" control % F cells/erythrocytes (e.g., as compared to % F cells/erythrocytes of the patient prior to treatment, e.g., as compared to the average % F cells/erythrocytes of a patient population not undergoing treatment (e.g., a healthy patient population)). For example, in some embodiments, the administering may expand % F cells in the subject by at least 5%, at least 8%, at least 10%, at least 15%, or at least 23% or more as compared to a baseline control. In some embodiments, the administering may expand % F cells in the subject by about 5% to about 30%, about 6% to about 24%, or by about 8% to about 20% as compared to a baseline control.

In some embodiments, the administering expands F cells to a total amount of at least 10% to at least 30% or more of total erythrocytes (e.g., at least 15%, 16%, 17%, 18%, 19%, 20%, 21%, 22%, 23%, 24%, 25%, 26%, 27%, 28%, 29%, or 30% or more F cells/erythrocytes or any value or range therein) per sample (e.g., in a patient blood sample). For example, in some embodiments, the administering may expand F cells to a total amount of at least 15%, at least 20%, at least 23%, at least 35% or more of total erythrocytes in a sample. In some embodiments, the administering may expand F cells to a total amount of about 15% to about 30%, about 18% to about 25%, or about 15% to about 35%, of total erythrocytes in a sample.

In some embodiments of the methods of the present invention, the subject may be a mammal. In some embodiments of the methods of the present invention, the subject may be a human.

Administration of the compounds or composition of the invention may be via any accepted mode known to one skilled in the art, for example, orally, parenterally, by inhalation spray, topically, rectally, nasally, buccally, vaginally, intraocularly, intrapulmonarily, or via an implanted reservoir. The term "parenterally" includes without limitation subcutaneously, intravenously, intramuscularly, intraperitoneally, intrathecally, intraventricularly, intrasternally, intracranially, intratumorally, by injection into a blood vessel feeding a tumor, by intraosseous injection and by infusion techniques. In some embodiments, the CDA substrate drug and cedazuridine may be administered intravenously, orally, and/or subcutaneously.

The administering of (i) and (ii) in the methods of the present invention may be performed prior to, at substantially the same time with, or after one another. In some embodiments of the methods of the present invention, the administering of (i) is concurrent with the administering of (ii). The term "concurrent" as used herein encompasses wherein the administering of (i) may be immediately followed by the administering of (ii), and/or wherein the administering of (ii) may be immediately followed by the administering of (i) (e.g., at substantially the same time, e.g., less than 30 minutes, e.g., less than 30, 25, 20, 15, 10, 5 or less minutes apart). The term "concurrent" as used herein also encompasses wherein the administering of (i) and (ii) is performed together, e.g., concomitant, e.g., in a single (e.g., combined) composition.

In some embodiments, the administering of (i) may be performed prior to the administering of (ii) (e.g., within 1, 2, 3, 4, 5, 6, 7, 8, 9, 10, 11, or 12 hrs). In some embodiments, the administering of (ii) is performed prior to the administering of (i) (e.g., within 1, 2, 3, 4, 5, 6, 7, 8, 8, 9, 10, 11, or 12 hrs). In some preferred embodiments, the administering of (i) may be performed prior to the administering of (ii) within, e.g., 1, 2, or 3 hrs. In some preferred embodiments, the administering of (ii) may be performed prior to the administering of (i) within, e.g., 1, 2, or 3 hrs.

Any administration regimen well known to those skilled in the art for regulating the timing and sequence of drug delivery can be used and repeated as necessary to effect treatment in the methods of the invention. For example, the compounds or composition of the invention may be administered 1, 2, 3 or 4 times daily, by a single dose, multiple discrete doses or continuous infusion. In some embodiments, the administering of (i) and (ii) may be performed about 1 day to about 28 days per 28-day cycle (e.g., about 1, 2, 3, 4, 5, 6, 7, 8, 9, 10, 11, 12, 13, 14, 15, 16, 17, 18, 19, 20, 21, 22, 23, 24, 25, 26, 27, or 28 days per 28-day cycle). In some embodiments, the administering of (i) and (ii) may be performed on consecutive days per 28-day cycle. For example, (i) and (ii) may be administered on any 2 consecutive days. In some embodiments, (i) and (ii) may be administered on any 3 consecutive days (e.g., on a Monday, Tuesday, and a Wednesday "MTW"; on a Tuesday, Wednesday, and a Thursday "TWTh"; on a Wednesday, Thursday, and a Friday "WThF"; on a Thursday, Friday, and Saturday "ThFS"; on a Friday, Saturday, and a Sunday "FSS"; on a Saturday, Sunday, and a Monday "SSM"; and/or on a Sunday, Monday, and a Tuesday "SMT", etc.). In some embodiments, the administering of (i) and (ii) may be performed on 5 consecutive days (e.g., MTWThF or any other combination of 5 consecutive days), on 7 consecutive days (MTWThFSS or any other combination of 7 consecutive days), on 14 consecutive days (e.g., two consecutive weeks); 21 consecutive days (e.g., three consecutive weeks), and/or on 28 consecutive days (e.g., four consecutive weeks) per 28-day cycle. The consecutive day treatments may be repeated one or more times per 28-day cycle, e.g., every week, every other week.

In some embodiments, the administering of (i) and (ii) may be performed on non-consecutive days per 28-day cycle, e.g., for 1, 2, 3, 4, 5, 6, 7, 8, 9, 10, 11, 12, 13, 14, 15, 16, 17, 18, 19, 20, 21, 22, 23, 24, 25, 26, or 27 or more non-consecutive days. Non-consecutive days may comprise a schedule of every-other day, (e.g., MWF), every two days, every three days, every four days, every five days, every six days, every seven days, etc. in a 28-day cycle. Non-consecutive days may comprise administering for a number of consecutive days (e.g., "on"), followed by a number of days without administering (e.g., "off"), followed by administering for a number of consecutive days (e.g., "on"), etc., within a 28-day cycle. For example, in some embodiments, the administering may be performed on 2 non-consecutive days (e.g., every Monday and Friday or any other combination of 2 non-consecutive days). In some embodiments, the administering may be performed on 3 non-consecutive days (e.g., MWF or any other combination of 3 non-consecutive days). The non-consecutive day treatments may be repeated one or more times per 28-day cycle, e.g., every week, every other week.

In some embodiments, the administering may be performed, e.g., for 10 total days per 28-day cycle, wherein the 10 days of administering comprise 5 consecutive days administering (e.g., 5 days "on"), followed by 2 consecutive days without administering (e.g., 2 days "off"), followed by 5 consecutive days administering (e.g., 5 days "on"), per 28-day cycle. In some embodiments, the administering may be performed, e.g., for 14 total days, wherein the 14 days of administering comprise 7 days "on" followed by 7 days "off" followed by 7 days "on", per 28-day cycle. In some embodiments, the administering may be performed, e.g., for 9 total days, wherein the 9 days of administering comprise 3 consecutive days "on" followed by 4 consecutive days "off", followed by 3 consecutive days "on" followed by 4 consecutive days "off", followed by 3 consecutive days "on", per 28-day cycle. In some embodiments, the administering may be performed, e.g., for 9 total days, wherein the 9 days of administering comprise 3 non-consecutive days "on" (e.g., MWF), followed by 1 day "off", followed by 3 non-consecutive days "on" (e.g., MWF), followed by 1 day "off", followed by 3 non-consecutive days "on", per 28-day cycle.

In some embodiments, the administering steps (i) and (ii) may be performed for one or more weeks per 28-day cycle, e.g., one week, two weeks, three weeks, or four weeks per 28-day cycle. The weeks may be consecutive and/or non-consecutive.

The administration regimen may include pretreatment and/or co-administration with at least one additional therapeutic agent. In such case, the compounds or composition of the invention, CDA substrate drug and/or at least one additional therapeutic agent may be administered simultaneously, separately, or sequentially.

Examples of a chemotherapeutic agent include without limitation: alkylating agents (e.g., which may include doxorubicin, cyclophosphamide, estramustine, carmustine, mitomycin, bleomycin and the like); antimetabolites (e.g., which may include 5-Fluoro-Uracil, capecitabine, gemcitabine, nelarabine, fludarabine, methotrexate and the like); platinating agents (e.g., which may include cisplatin, oxaliplatin, carboplatin and the like); topoisomerase inhibitors (e.g., which may include topotecan, irinotecan, etoposide and the like); tubulin agents (e.g., which may include paclitaxel, docetaxel, vinorelbine, vinblastine, vincristine, other taxanes, epothilones, and the like); signaling inhibitors (e.g., kinase inhibitors, antibodies, farnesyltransferase inhibitors, and the like); and other chemotherapeutic agents (e.g., tamoxifen, anti-mitotic agents such as polo-like kinase inhibitors or aurora kinase inhibitors, and the like).

Examples of administration regimens include, without limitation: administration of each compound, composition, CDA substrate drug, and/or therapeutic agent in a sequential manner; and co-administration of each compound, composition, CDA substrate drug, and/or therapeutic agent in a substantially simultaneous manner (e.g., as in a single unit dosage form) or in multiple, separate unit dosage forms for each compound, composition, CDA substrate drug, and/or therapeutic agent.

It will be appreciated by those skilled in the art that the "effective amount" or "dose level" will depend on various factors such as the particular administration mode, administration regimen, compound, and composition selected, and the particular disease and patient being treated. For example, the appropriate dose level may vary depending upon the activity, rate of excretion and possible toxicity of the specific compound or composition employed; the age, body weight, general health, gender and diet of the patient being treated; the frequency of administration; the other therapeutic agent(s) being co-administered; and the type and severity of the disease.

The present invention contemplates per dose amounts on the order of about 5 mg to about 35 mg per dose of decitabine or the equivalent amount of other CDA substrate drugs. As used herein, the term "equivalent amount" refers to any dose amount that results in equivalent efficacy, such as equivalent epigenetic effects (e.g., LINE-1 demethylation, e.g., % F cell expansion) and/or equivalent reduction of myelosuppressive effects (e.g., neutropenia).

In some embodiments, the dose of decitabine may be about 5, 10, 15, 20, 25, 30, or 35 mg per dose, or any value or range therein. In some embodiments, the dose of decitabine may be less than about 35, 30, 25, 20, 15, or 10 mg. The present invention further contemplates cumulative dose amounts on the order of about 15 mg to about 150 mg cumulative per 28-day cycle of treatment of decitabine or the equivalent amount of other CDA substrate drugs (e.g., about 10 mg to about 450 mg 5-azacytidine). In some embodiments, the cumulative dose of decitabine per 28-day cycle may be, e.g., about 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 146, 147, 148, 149, or 150 mg or any value or range therein. For example, in some embodiments, the amount of decitabine per dose may be about 5 mg to about 35 mg, about 5 mg to about 30 mg, about 5 mg to about 25 mg, about 5 mg to about 20 mg, about 5 mg to about 15 mg, about 5 mg to about 10 mg, about 7 mg to about 20 mg, or about 5 mg, about 10 mg, about 15 mg, or about 35 mg. In some embodiments, the cumulative dose of decitabine per 28-day cycle may be, for example, about 15 mg to about 150 mg, about 15 mg to about 125 mg, about 15 mg to about 100 mg, about 15 mg to about 75 mg, about 15 mg to about 50 mg, about 15 mg to about 40 mg, about 15 mg to about 30 mg, about 30 mg to about 120 mg, about 45 mg to about 125 mg, about 50 mg to about 150 mg, about 65 mg to about 125 mg, or about 75 mg to about 140 mg. In some embodiments, the cumulative dose of decitabine per 28-day cycle may be, e.g., about 50 mg, or about 75 mg, or about 130 mg. Dose levels, mode of administration, and administration regimen may be modified by those skilled in the art using known techniques as judged necessary for the subject (e.g., the patient).

In some embodiments, the dose of 5-azacytidine may be about 10, 15, 20, 25, 30, 35, 40, 45, 50, 75, 100, 125, 150, 175, 200, 225, 250, 275, 300, 325, 350, 375, 400, 425, 430, 435, 440, 445, or 450 mg per dose, or any value or range therein. In some embodiments, the dose of 5-azacytidine may be less than about 450, 445, 440, 435, 430, 425, 400, 375, 350, 325, 300, 275, 250, 225, 200, 175, 150, 125, 100, 75, 50, 45, 40, 35, 30, 25, 20, 15, or 10 mg. The present invention further contemplates cumulative dose amounts on the order of about 15 mg to about 150 mg cumulative per 28-day cycle of treatment of decitabine or the equivalent amount of other CDA substrate drugs. In some embodiments, the cumulative dose of 5-azacytidine per 28-day cycle may be, e.g., about 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400 or 3500 mg or any value or range therein. For example, in some embodiments, the amount of 5-azacytidine per dose may be about 10 mg to about 35 mg, about 35 mg to about 400 mg, about 10 mg to about 450 mg, about 15 mg to about 420 mg, about 20 mg to about 350 mg, about 35 mg to about 300 mg, about 12 mg to about 150 mg, or about 25 mg, or about 250 mg. In some embodiments, the cumulative dose of 5-azacytidine per 28-day cycle may be, for example, about 10 mg to about 3500 mg, about 15 mg to about 3125 mg, about 15 mg to about 2940 mg, about 10 mg to about 1400 mg, about 200 mg to about 3500 mg, or about 50 mg to about 2750 mg. In some embodiments, the cumulative dose of 5-azacytidine per 28-day cycle may be, e.g., about 10 mg, about 200 mg, about 1400, about 2940, or about 3150 mg. Dose levels, mode of administration, and administration regimen may be modified by those skilled in the art using known techniques as judged necessary for the subject (e.g., the patient).

The present invention contemplates per dose amounts on the order of about 40 mg to about 1000 mg per dose of cedazuridine. In some embodiments, the dose may be about 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 925 mg, 950 mg, 975 mg or 1000 mg per dose, or any value or range therein. For example, in some embodiments, the dose amount may be about 100 mg per dose of cedazuridine. In some embodiments, the dose amount may be less than about 100 mg of cedazuridine. The present invention further contemplates cumulative dose amounts on the order of about 40 mg to about 7000 mg cumulative per 28-day cycle of treatment of cedazuridine. In some embodiments, the cumulative dose per 28-day cycle may be, e.g., about 40, 50, 100, 125, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 6925, 6950, 6975, or 7000 mg or any value or range therein. For example, in some embodiments, the cumulative dose of cedazuridine per 28-day cycle may be, for example, about 40 mg to about 150 mg, about 65 mg to about 3500 mg, about 75 mg to about 6500 mg, about 40 mg to about 500 mg, about 100 mg to about 250 mg, or about 75 mg to about 1000 mg. In some embodiments, the cumulative dose of cedazuridine per 28-day cycle may be, e.g., about 100 mg, about 1000 mg, about 725 mg, about 2000 mg, about 6500 mg, about 3500 mg, about 2500 mg, about 4750 mg, or about 475 mg. Dose levels, mode of administration, and administration regimen may be modified by those skilled in the art using known techniques as judged necessary for the subject (e.g., the patient).

Formulations and Kits

The pharmaceutical compositions (e.g., compound, composition, CDA substrate drug, and/or therapeutic agent) of the invention may be formulated for administration in solid or liquid form, including those adapted for the following: (1) oral administration, for example, drenches (for example, aqueous or non-aqueous solutions or suspensions), tablets (for example, those targeted for buccal, sublingual and systemic absorption), caplets, boluses, powders, granules, pastes for application to the tongue, hard gelatin capsules, soft gelatin capsules, mouth sprays, troches, lozenges, pellets, syrups, suspensions, elixirs, liquids, emulsions and microemulsions; (2) parenteral administration, for example, by subcutaneous, intramuscular, intravenous or epidural injection as, for example, a sterile solution or suspension; (3) topical application, for example, as a cream, ointment, patch, pad or spray applied to the skin; (4) intravaginally or intrarectally, for example, as a pessary, cream or foam; (5) sublingually; (6) ocularly; (7) transdermally; or (8) nasally. The pharmaceutical compositions may be formulated for immediate, sustained or controlled release.

In some embodiments, the pharmaceutical compositions are formulated for oral administration. In further embodiments, the pharmaceutical compositions are formulated for oral administration in solid form.

Pharmaceutical compositions of the invention can be prepared using known materials and techniques, which may include but are not limited to mixing and/or blending the compound of the invention with the pharmaceutically acceptable excipient and optional therapeutic agent(s).

Another aspect of the present invention relates to a unit dosage form and a kit comprising at least one unit dosage form, which unit dosage form comprises a compound or pharmaceutical composition of the invention. In some embodiments, the unit dosage form comprises about 5, 10, 15, 25, 20, 30, or 35 mg decitabine or an equivalent amount of another CDA substrate drug (e.g., about 10, 15, 20, 25, 30, 35, 40, 45, 50, 75, 100, 125, 150, 175, 200, 225, 250, 275, 300, 325, 350, 375, 400, 425, 430, 435, 440, 445, or 450 mg 5-azacytidine). In some embodiments, the unit dosage form of decitabine may comprise less than about 35, 30, 25, 20, 15, or 10 mg. For example, in some embodiments, the unit dosage form of decitabine may be about 5 mg to about 35 mg, about 5 mg to about 30 mg, about 5 mg to about 25 mg, about 5 mg to about 20 mg, about 5 mg to about 15 mg, about 5 mg to about 10 mg, about 7 mg to about 20 mg, or about 5 mg, about 10 mg, about 15 mg, or about 35 mg. In some embodiments, the unit dosage form of 5-azacytidine may be about 10 mg to about 35 mg, about 35 mg to about 400 mg, about 10 mg to about 450 mg, about 15 mg to about 420 mg, about 20 mg to about 350 mg, about 35 mg to about 300 mg, about 12 mg to about 150 mg, or about 25 mg, or about 250 mg. In some embodiments, the unit dosage form of cedazuridine comprises about 40 mg to about 1000 mg cedazuridine. For example, in some embodiments, the unit dosage form of cedazuridine may comprise about 40 mg, about 75 mg, about 100 mg, about 200 mg, about 100 mg, about 750 mg, about 500 mg, or about 250 mg cedazuridine. In some embodiments, the unit dosage form of cedazuridine may be less than about 100 mg. In some embodiments, the unit dosage form comprises a CDA substrate drug (e.g., decitabine, e.g., 5-azacytidine) in the amount described above and cedazuridine in the amount described above.

The kit may further comprise a container and/or a package suitable for commercial sale. The container can be in any conventional shape or form as known in the art which is made of a pharmaceutically acceptable material, such as a paper or cardboard box, a glass or plastic bottle or jar, a re-sealable bag, or a blister pack with individual dosages for pressing out of the pack according to a therapeutic schedule. More than one container can be used together in a single package. For example, tablets may be contained in a blister pack which is in turn contained within a box.

The kit may further comprise information. The information may be provided on a readable medium. The readable medium may comprise a label. The information may be directed towards a physician, pharmacist or patient. The information may indicate that the unit dosage form may cause one or more adverse effects. The information may comprise instructions for administering the unit dosage form, such as in a manner described herein. These instructions may be provided in a variety of ways. For example, the information may include a table including a variety of weights or weight ranges and appropriate dosages for each weight or weight range.

The information can be associated with the container, for example, by being: written on a label (e.g., the prescription label or a separate label) adhesively affixed to a container; included inside a container as a written package insert;

applied directly to the container such as being printed on the wall of a box or blister pack; or attached as by being tied or taped, for example as an instructional card affixed to the neck of a bottle via a string, cord or other line, lanyard or tether type device.

It will be apparent to those skilled in the art that specific embodiments of the present invention may be directed to one, some or all of the above-indicated aspects as well as other aspects, and may encompass one, some or all of the above- and below-indicated embodiments, as well as other embodiments.

Other than in the working examples, or where otherwise indicated, all numbers expressing quantities of ingredients, reaction conditions, and so forth used in the specification and claims are to be understood as being modified by the term "about". Accordingly, unless indicated to the contrary, such numbers are approximations that may vary depending upon the-desired properties sought to be obtained by the present invention. At the very least, and not as an attempt to limit the application of the doctrine of equivalents to the scope of the claims, each numerical parameter should be construed in light of the number of significant digits and ordinary rounding techniques.

While the numerical ranges and parameters setting forth the broad scope of the invention are approximations, the numerical values set forth in the working examples are reported as precisely as possible. Any numerical value, however, inherently contains certain errors necessarily resulting from the standard deviation found in their respective testing measurements.

Having described the present invention, the same will be explained in greater detail in the following examples, which are included herein for illustration purposes only, and which are not intended to be limiting to the invention.

EXAMPLES

Example 1: Evaluation of Low Dose Combination Decitabine/Cedazuridine Systems Pharmacology Model Decitabine (DAC) is a well characterized hypomethylating agent (HMA) which is incorporated into DNA during the S-phase of cell cycle, inhibiting methylation of antitumor genes and inducing G2/M arrest. Decitabine is approved for treatment of intermediate to high risk MDS, but is rapidly degraded by cytidine deaminase (CDA), resulting in poor oral decitabine bioavailability and systemic exposures. ASTX727 as a fixed dose oral combination of the CDA inhibitor E7727 and decitabine has been tested for the treatment of patients with intermediate- and high-risk MDS or chronic myelomonocytic leukemia (CMML). Low risk MDS (e.g., IPSS low or IPSS Intermediate-1) patients present with less than 5% leukemic blasts in bone marrow and anemia or cytopenia. As treatment with decitabine causes side effects such as neutropenia and/or thrombocytopenia, the objective of this study was to use quantitative systems pharmacology (QSP) modeling to describe the effect of decitabine on neutrophils and simulate regimens to minimize myelosuppression.

A QSP model was previously developed describing myeloblasts cell cycle, leukemic blasts, neutrophils and platelets in physiological compartments (e.g., bone marrow and blood), and PK of decitabine after i.v. infusion, and was applied to model dosing with subcutaneous guadecitabine (SGI-110, a dinucleotide of decitabine linked to deoxyguanosine; 2015 ASCPT: Systems Pharmacology Modeling for Hypomethylating agents Decitabine and SGI-110 for Evaluation of AML treatment by targeting the S-phase with prolonged Pharmacokinetic exposures, Oganesian et al., O) and to model oral ASTX727 (2017 ASCPT: Development of a Semi-Mechanistic PK/PD Model of an Oral Fixed Dose Combination (FDC) of Cytidine Deaminase Inhibitor E7727 with Decitabine (ASTX727) in Subjects with Myelodysplastic Syndromes, Burroughs et al.). The present model describes myeloblasts cell cycle, leukemic blasts, neutrophils and platelets in physiological compartments (e.g., bone marrow and blood), PK of decitabine, and PD marker of LINE-1 demethylation changes following treatment with HMAs, as well as effects of decitabine on leukemic cells, neutrophils and platelets to model various low-dose combinations of decitabine/cedazuridine.

Figure 2:
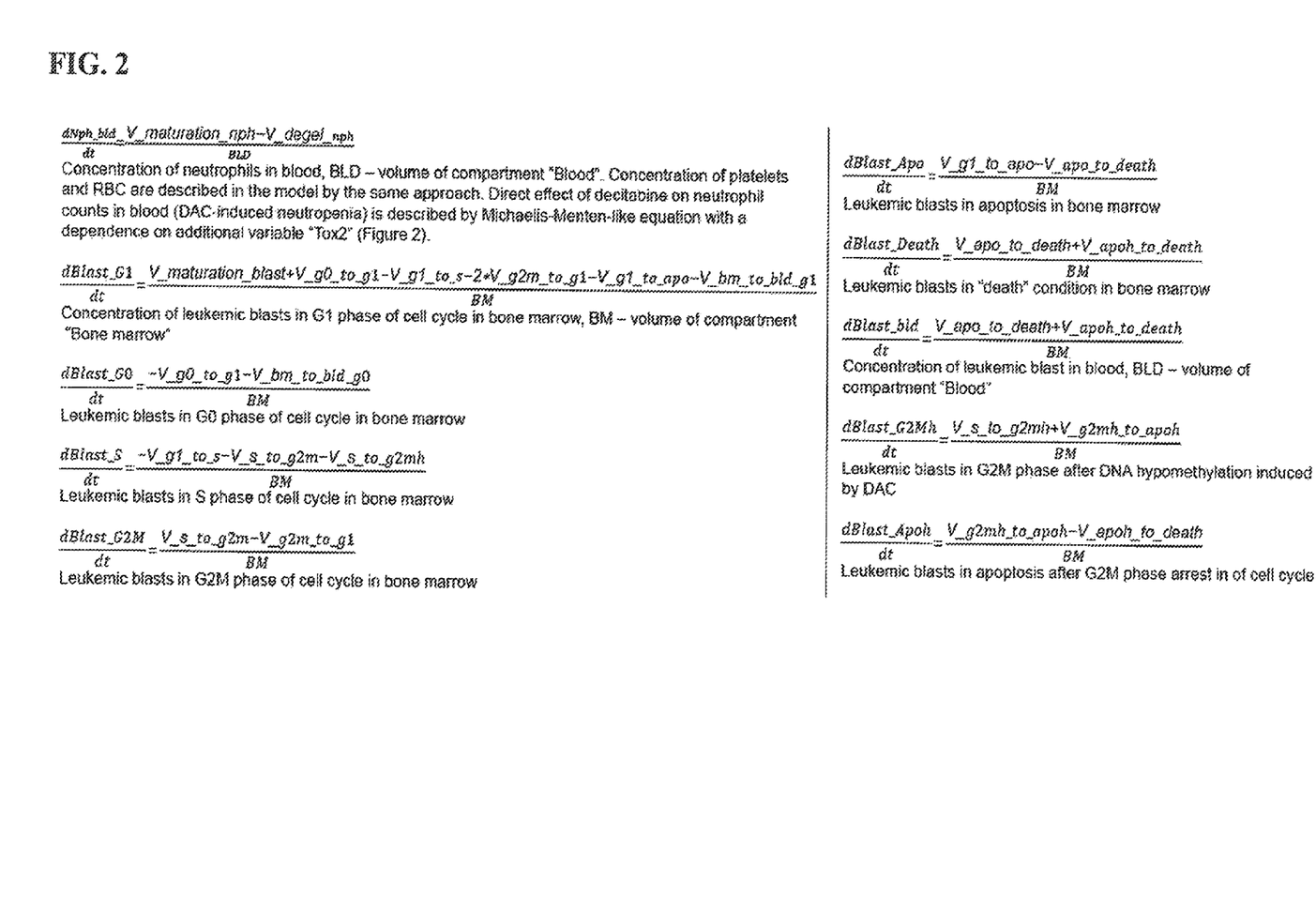
FIG. 2 shows key differential equations used in the quantitative systems pharmacology model as described in Example 1.

Key differential equations for the model include those shown in FIG. 2.

Figure 1:
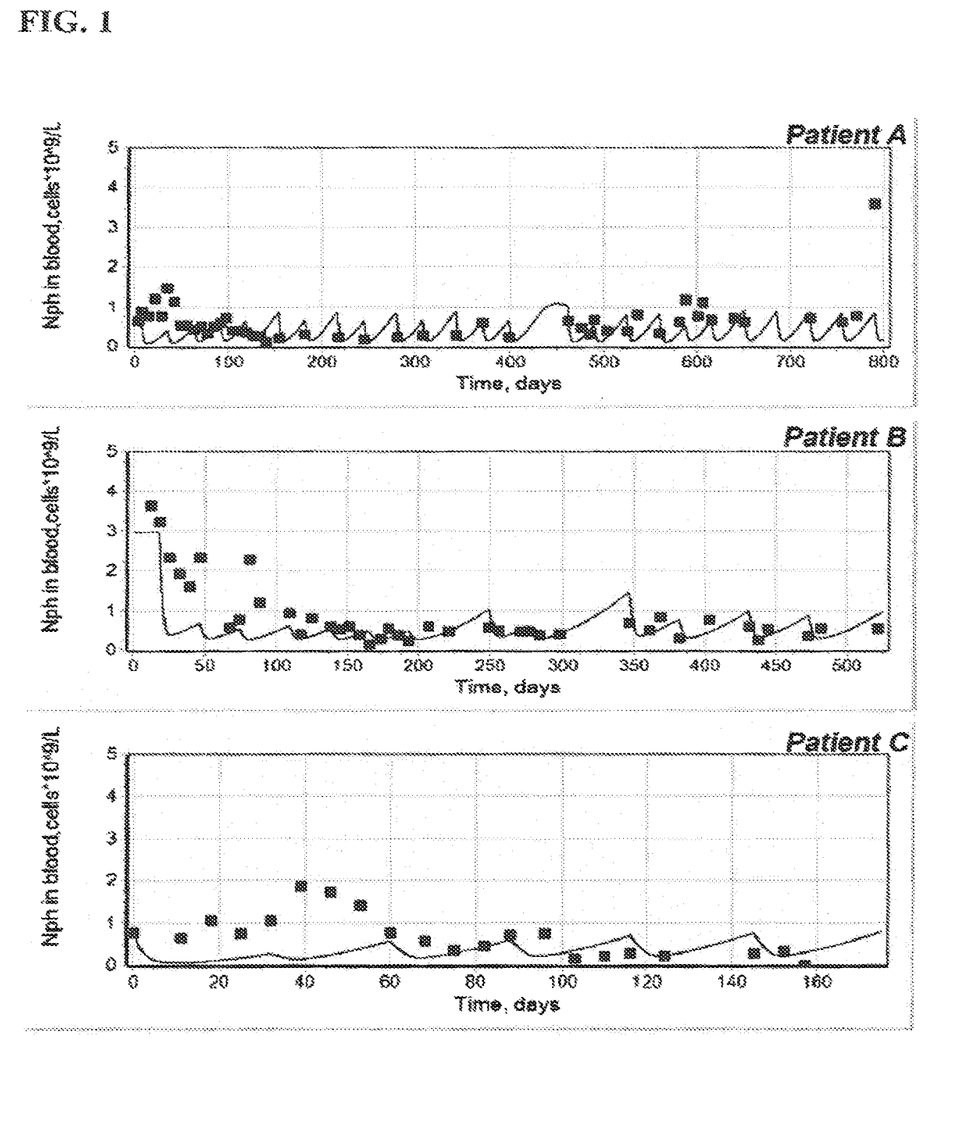
FIG. 1 shows neutrophil dynamics in three patients after guadecitabine treatment of AML patients ("responders") using daily dosing on 5 consecutive days every 28 days. Fitting results, observed vs. predicted.

For this study, the model was successfully calibrated and validated against various types of data and successfully reproduced clinical data on neutrophil counts following treatment with guadecitabine in AML patients (FIG. 1). Thus, the model showed that decitabine-induced neutropenia is not the result of gene demethylation or decitabine incorporation into DNA, but has a complex mechanism that depends on decitabine levels in plasma.

Figure 3A:
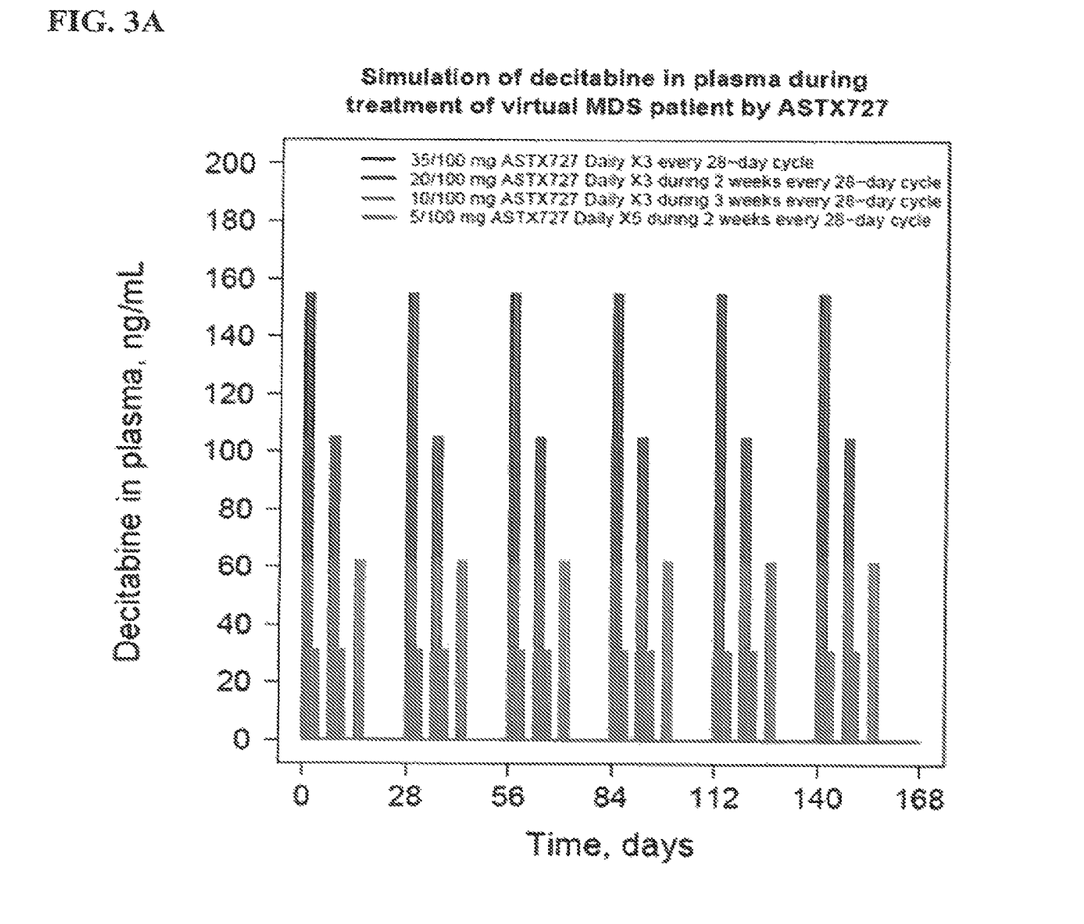
FIGS. 3A-3B show simulations of decitabine in plasma (FIG. 3A) and neutrophil dynamics (FIG. 3B) during treatment of virtual MDS patients with varying regimens of ASTX727. Regimens simulated included: (black) 35 mg decitabine and 100 mg cedazuridine ("35/100 mg ASTX727") daily for 3 consecutive days every 28-day cycle; (blue) 20 mg decitabine and 100 mg cedazuridine ("20/100 mg ASTX727") daily for 3 consecutive days during two weeks (6 days total) every 28-day cycle; (red) 10 mg decitabine and 100 mg cedazuridine ("10/100 mg ASTX727") daily for 3 consecutive days during three weeks (9 days total) every 28-day cycle; and (green) 5 mg decitabine and 100 mg cedazuridine ("5/100 mg ASTX727") daily for 5 consecutive days during two weeks (10 days total) every 28-day cycle.
Figure 3B:
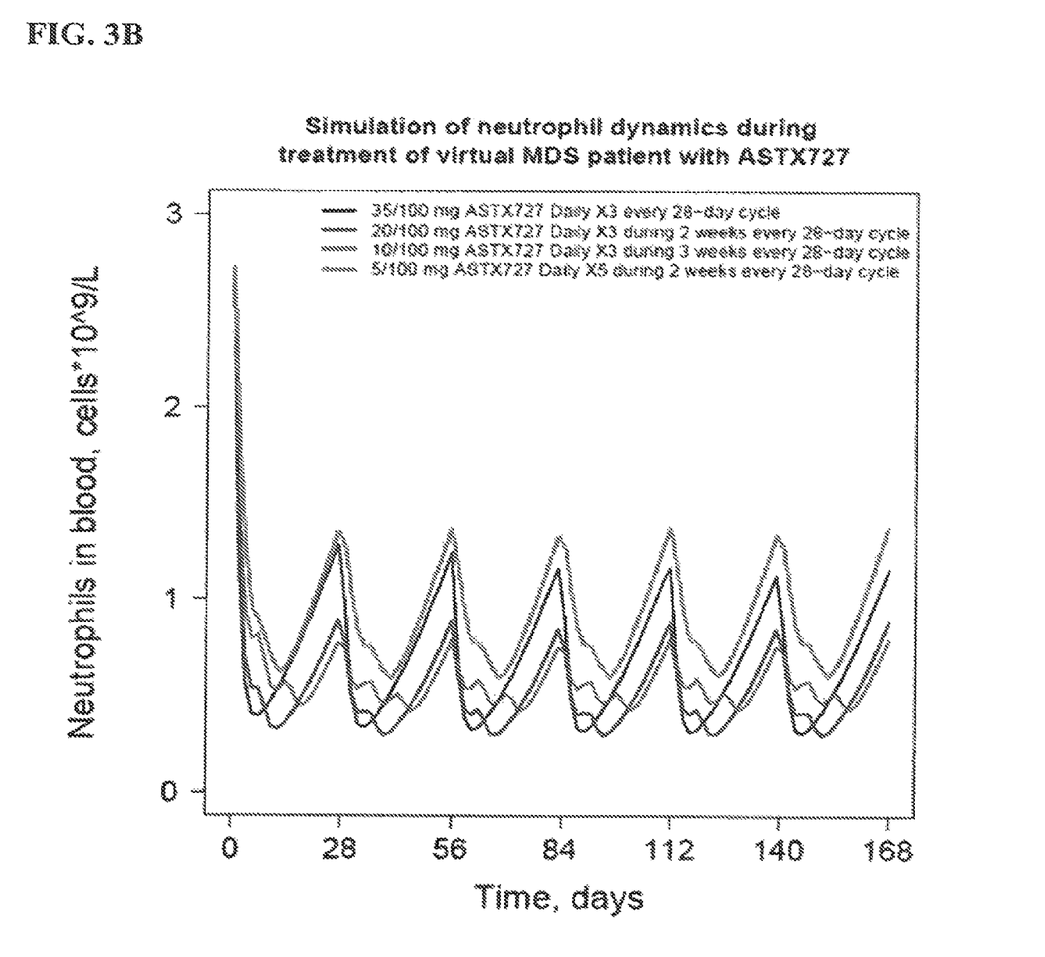

Simulations with several regimens using low doses of decitabine for ASTX727 administration were performed. The model predicted that neutrophil levels depend on the dose and frequency of ASTX727 administration (FIGS. 3A-3B). The model further suggested that the least toxic ASTX-LD regimen among those simulated was the 5 mg DAC/100 mg E7727 daily (e.g., "5/100 mg") for 5 days for 2 weeks, repeated every 28-day cycle. ASTX727-LD regimens of 10/100 mg daily for 3 days for 3 weeks, and 20/100 mg daily for 3 days for 2 weeks had a similar effect on neutrophil dynamics, whereas the effect on leukemic blasts was better with the 10/100 mg daily for 3 days for 3 weeks regimen.

Thus, the updated model adequately described available data on neutrophil dynamics after treatment with guadecitabine, and allowed simulation of lower doses of varying regimens for optimization of treatment with ASTX727 to minimize decitabine-mediated adverse effects such as neutropenia and potentially maximize efficacy. The model suggested that the optimal regimen of ASTX727 that induces minimal changes in neutrophil counts and with potential maximal effects on leukemic blasts in the bone marrow modeled was a low dose of 5 mg decitabine with 100 mg E7727, dosed daily for 5 days for 2 weeks of every 28-day cycle.

Example 2: Low Dose Combination Decitabine/Cedazuridine with Extended Schedule in Subjects with Lower Risk MDS A Phase 1-2, multicenter, open-label study of various combination decitabine/cedazuridine (referred to as ASTX727) low dose (LD) doses and schedules was performed to assess the safety, pharmacodynamics, pharmacokinetics, and hematologic response in subjects with an International Prognostic Scoring System (IPSS) risk category of low-risk or Intermediate-1 (Int-1) MDS.

Inclusion criteria included men or women 18 or older with IPSS low risk or Int-1 MDS, an Eastern Cooperative Oncology Group (ECOG) status of 0 to 2, adequate hepatic and renal function, as well as at least either a red blood cell transfusion dependence of 2 or more units of RBCs or hemoglobin of less than 8.5 g/dL at baseline, an ANC of less than $0.5 \times 10^9$/L prior to enrollment, or platelet counts of less than $50 \times 10^9$/L prior to enrollment.

Exclusion criteria included prior treatment of other investigational drugs or therapy within 2 weeks before study, or 5 half-lives, whichever longer; prior treatment of MDS concluded less than 1 month prior to study; diagnosis of CMML; uncontrolled systemic diseases or active uncontrolled infections, known mental illness or substance abuse/addiction; life-threatening illness; active infection of HIV or hepatitis; or other prior malignancy unless the subject has been disease free for at least 1 year.

Randomization was stratified by diagnostic category (low risk vs. Int-1 IPSS), baseline ANC ($\leq 10^9$/L vs. $\geq 10^9$/L), and ECOG Performance Score (0-1 vs. 2). Phase 1 Stage A subjects were randomized in a 1:1:1 ratio into three cohorts of 6 subjects, each in a 10-day schedule in a 28-day cycle, as shown in Table 1.

included % LINE-1 methylation change from baseline, area under the curve (AUC), maximum plasma concentration (Cmax), time to reach maximum concentration (Tmax), half-life (t1/2), hematologic response, treatment time required for bone marrow blasts to expand by $\geq 50\%$ and/or to greater than 5% of total sample cells, as well as leukemia-free survival and overall survival.

The 5 mg cohort showed 2 patients that experienced neutropenia of greater than two weeks or to a level leading to dose interruption. The 10 mg cohort showed three patients with neutropenia of greater than two weeks. Hemoglobin levels, platelet counts, and ANC of the 5 mg cohort and 10 mg cohort were analyzed.

Figure 4:
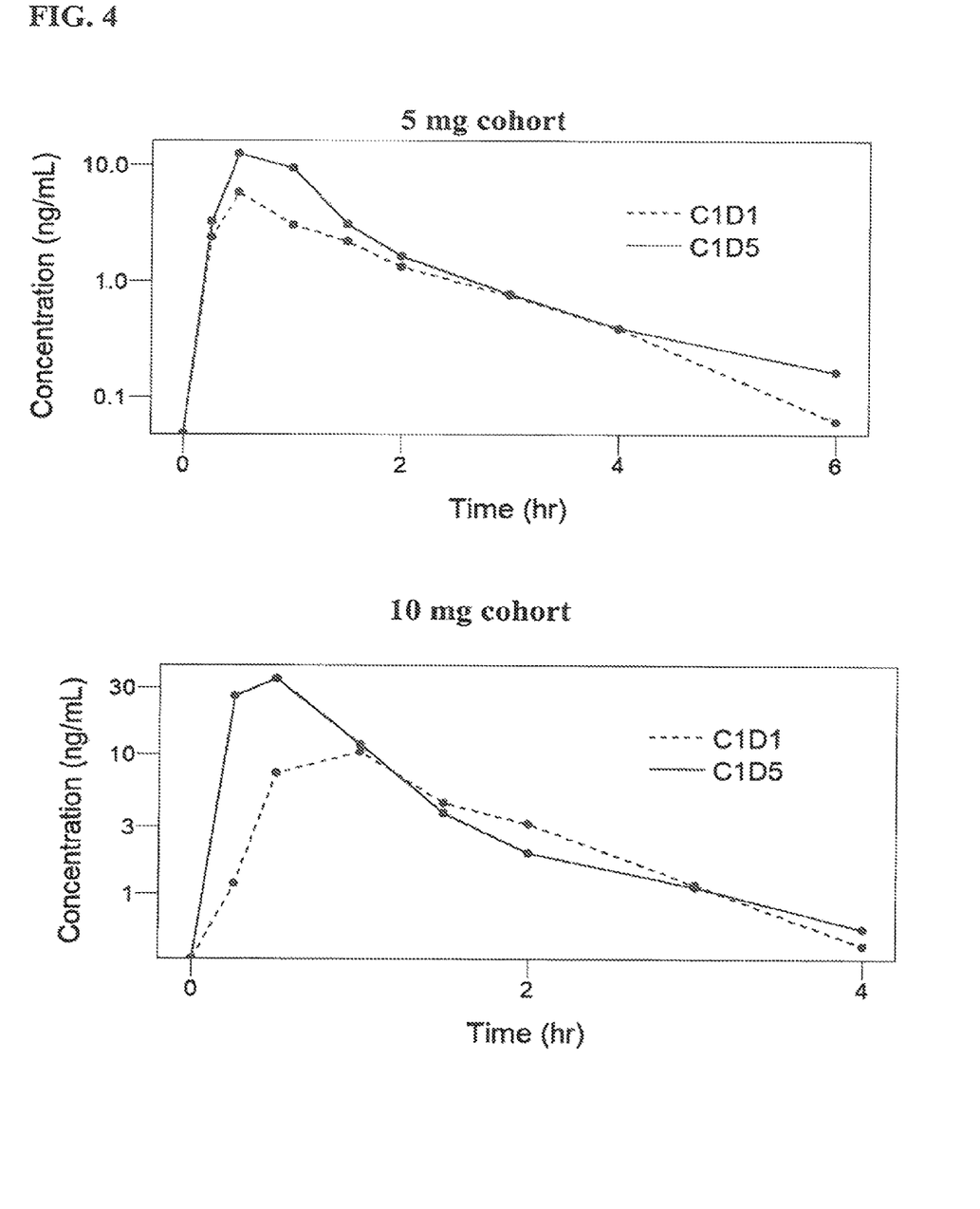
FIG. 4 shows decitabine concentrations detectable in patient plasma at indicated time points. C1D1 refers to cycle 1, day 1; C1D5 refers to cycle 1, day 5. Data is cumulative of patients in the 5 mg cohort (top panel) and 10 mg cohort (bottom panel) identified in Table 1.

Treatment showed LINE-1 demethylation as well as hemoglobin-F carrying cell expansion ("F cells") in both the 5 mg and 10 mg cohorts, indicators of epigenetic effects. An F cell percentage of greater than 20% is also used as a correlative with clinical effect in the sickle cell field. Mean decitabine concentrations in plasma are shown in FIG. 4. Decitabine concentrations were detectable in plasma up to four to six hours for the 5 and 10 mg cohorts. Mean PK parameters are shown in Table 2. There was an approximate 2-fold increase in exposures from day 1 to day 5, and from 5 mg to 10 mg. Comparisons of total cycle area under the curve (AUC) are shown in Table 3.

TABLE 1

Phase 1 Stage A Cohorts (10-day Schedule)

| Cohort (n = 6 each) | Decitabine Dose (mg) | Cedazuridine Dose (mg) | Schedule (28-Day Cycle) | Total Cedazuridine Dose (mg/cycle) | Total Decitabine Dose (mg/cycle) |
|---|---|---|---|---|---|
| 1 | 5 | 100 | Daily × 5, Off × 2, Daily × 5 | 1000 | 50 |
| 2 | 10 | | | | 100 |
| 3 | 15 | | | | |

An additional cohort of 15 mg decitabine and 100 mg cedazuridine was also contemplated. The goal of this study was to find a dose and schedule of ASTX727 LD which provides active epigenetic and clinical effects with minimum myelosuppression. All daily doses were lower than previously tested. The cumulative doses/cycle of decitabine were less than the approved regimen. The cumulative dose/cycle of cedazuridine was increased in Stage 1 and 2 of dose escalation over previously tested doses. Patient read-outs

TABLE 2

PK Parameters.

| | Occasion | N | $C_{max}$[1] (ng/mL) | $T_{max}$[2] (hr) | $AUC_{0-24 h}$[1] (ng*hr/mL) |
|---|---|---|---|---|---|
| Cohort 1 (5 mg) | C1D1 | 10 | 6.1 (76) | 0.5 (0.25-1.5) | 6.3 (70) |
| | C1D5 | 10 | 12.6 (85) | 0.5 (0.25-1.5) | 12.1 (64) |
| Cohort 2 (10 mg) | C1D1 | 4 | 12.2 (66) | 1.0 (0.5-2.0) | 13.2 (36) |
| | C1D5 | 3 | 31.0 (80) | 0.5 (0.25-0.5) | 26.3 (64) |

TABLE 3

Total Cycle AUC Comparison.

| Cohort | Daily decitabine dose (mg) | Cycle cumulative dose (mg) | % FDC cycle cumulative dose | Total cycle $AUC_{0-24 h}$ (ng*hr/mL) | % FDC total cycle $AUC_{0-24 h}$ |
|---|---|---|---|---|---|
| 1 | 5 | 50 | 29% | 115.2 | 14% |
| 2 | 10 | 100 | 57% | 249.9 | 30% |
| Standard dose[1] | 35 | 175 | 100% | 823.1 | 100% |

The LINE-1 demethylation and hemoglobin F (HbF) induction results indicate that the doses tested exerted epigenetic effects in a dose-responsive manner. Hypomethylation of LINE-1 observed in the 10 mg cohort showed higher magnitude achieved by higher risk MDS patients given higher doses in early phase studies.

Example 3: Additional Schedules for Low Dose Combination Decitabine/Cedazuridine with Extended Schedule in Subjects with Lower Risk MDS Patients are enrolled in cohorts of 5 mg or 10 mg of varying schedules per 28-day cycle, as shown in Tables 4 and 5.

TABLE 4

Cohorts on 3-day or 5-day treatment schedules.

| Cohort N = 6 each | Decitabine Dose (mg) | Cedazuridine Dose (mg) | Schedule (28-day cycle) | Total Cedazuridine Dose (mg/cycle) | Total Decitabine Dose (mg/cycle) |
|---|---|---|---|---|---|
| 1 | 5 | 100 | MWF 1 w on/1 w off | 600 | 30 |
| 2 | 10 | | MWF 1 w on/1 w off | 600 | 60 |
| 3 | 5 | | MWF 3 w on/1 w off | 900 | 45 |
| 4 | 10 | | MWF 3 w on/1 w off | 900 | 90 |
| 5 | 5 | | Daily × 5 | 500 | 25 |
| 6 | 10 | | Daily × 5 | 500 | 50 |

TABLE 5

Cohorts on 7-day or 14-day treatment schedules.

| Cohort (n = 6 each) | Decitabine Dose (mg) | Cedazuridine Dose (mg) | Schedule (28-Day Cycle) | Total Cedazuridine Dose (mg/cycle) | Total Decitabine Dose (mg/cycle) |
|---|---|---|---|---|---|
| 1 | 5 | 100 | Daily × 7, Off × 7, | 1400 | 70 |
| 2 | 10 | | Daily × 7, Off × 7 | | 140 |
| 3 | 5 | | Daily × 14, | | 70 |
| 4 | 10 | | Off × 14 | | 140 |

Additional schedules include a cohort receiving 20 mg of decitabine and 100 mg of cedazuridine for 5 days (e.g., 5 consecutive days) per 28-day cycle, a cohort receiving 10 mg of decitabine and 100 mg of cedazuridine for 7 days (e.g., 7 consecutive days) per 28-day cycle, and a cohort receiving 20 mg decitabine for 5 days (e.g., 5 consecutive days) per 28-day cycle, as well as a control group receiving 35 mg decitabine and 100 mg of cedazuridine for 3 days per 28-day cycle. Schedule changes in dosing amount (e.g., between 5 mg to 35 mg decitabine per dose), cumulative dosing, and administration (e.g., between 3 days to 21 days per 28-day cycle, given on consecutive days and/or non-consecutive days) are contemplated as well.

Dose-limiting toxicity is assessed to eliminate cohorts that experience the following events: (1) drug-related ≥Grade 3 non-hematologic events (except nausea, vomiting, or diarrhea well controlled by symptomatic treatment); (2) hematologic events (e.g., Grade 4 anemia, platelet, or ANC counts) not existing at baseline and lasting greater than 2 weeks in duration; and (3) drug-related toxicity causing delay of greater than 2 weeks after Cycle 1 to initiation of next scheduled cycle.

Example 4: Combination Decitabine/Cedazuridine Oral Vs. IV Delivery

Table 6 shows tabulated results of standard schedule treatment of oral combination decitabine/cedazuridine (ASTX727) resulted in greater levels of drug availability (by % AUC) in patients over those receiving decitabine and cedazuridine (E7727) intravenously.

TABLE 6

| | ASTX727 Oral Dose (mg) | | | 5-Days total $(AUC_{last})$ | | % of AUC |
|---|---|---|---|---|---|---|
| Cohort | DAC[1] | E7727 | N | Oral | IV | (Oral/IV) |
| 1 | 20 | 40 | 5[2] | 260 | 753 | 35% |
| 2 | 20 | 60 | 6 | 346 | 899 | 39% |
| 3 | 20 | 100 | 6 | 482 | 992 | 49% |
| 4 | 40 | 100 | 6 | 1120 | 775 | 144% |
| 5 | 30 | 100 | 19[3] | 701 | 852 | 85% |

[1]DAC oral dose not adjusted by weight or BSA;
[2]One significant outlier excluded from PK analysis;
[3]Includes 13 patient dose expansion.

Figure 5:
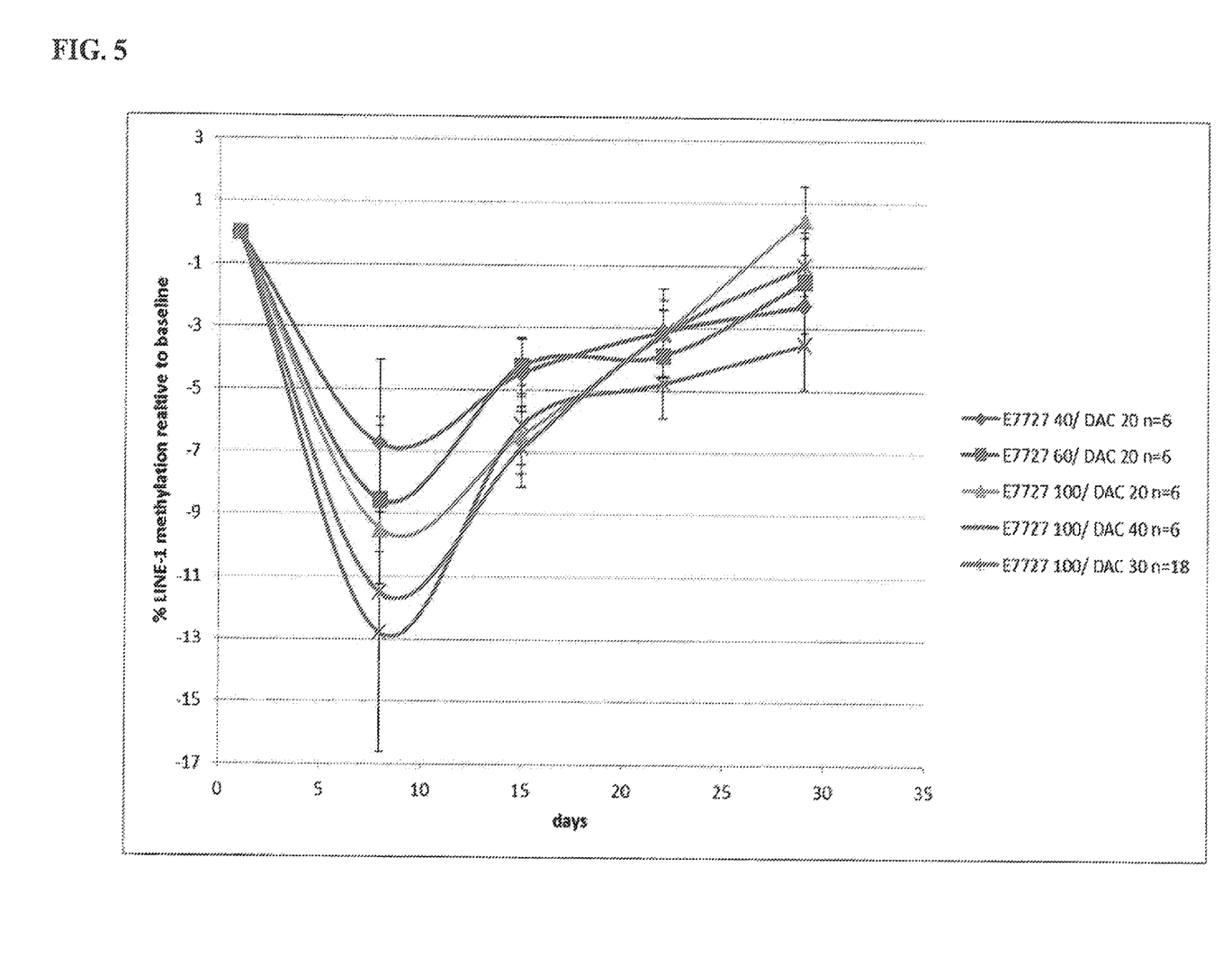
FIG. 5 shows % demethylation of LINE-1 achieved in the cohorts of Example 3. Groups identified in the figure legend correspond to the cohorts as listed in Table 6.

Cohort 4 oral delivered decitabine (DAC) at 40 mg exposure given with oral cedazuridine achieved and exceeded AUC of i.v. delivered decitabine at 20 mg/m² at an oral/i.v. ratio of 144%. Cohort 5 oral delivered decitabine at 30 mg given with oral cedazuridine exposure was 85% of i.v. delivered decitabine at 20 mg/m². Oral delivered decitabine dose of 35 mg in ASTX727 are expected to achieve an AUC of about 85% to about 140% of i.v. delivered decitabine. FIG. 5 shows % demethylation of LINE-1 achieved by the cohorts of Table 6. Cohorts 4 and 5 achieved LINE-1 demethylation from baseline of greater than 10%, comparable to historical data of i.v. delivered decitabine.

The foregoing examples are illustrative of the present invention, and are not to be construed as limiting thereof. Although the invention has been described in detail with reference to preferred embodiments, variations and modifications exist within the scope and spirit of the invention as described and defined in the following claims.

What is claimed is:

1. A method for inhibiting degradation of a cytidine deaminase (CDA) substrate drug in a subject in need thereof, comprising administering to the subject:
   (i) an effective amount of a CDA substrate drug, wherein when the CDA substrate drug is decitabine, the effective amount of decitabine is from about 5 mg per dose to about 15 mg per dose; and
   (ii) an effective amount of cedazuridine,
   thereby inhibiting degradation of the CDA substrate drug in the subject.

2. The method of claim 1, wherein the administering of (i) is concurrent with the administering of (ii).

3. The method of claim 2, wherein the administering is performed in one composition.

4. The method of claim 1, wherein the administering of (i) is performed prior to the administering of (ii).

5. The method of claim 1, wherein the administering of (ii) is performed prior to the administering of (i).

6. The method of claim 1, wherein the administering steps (i) and (ii) are performed about 1 day to about 28 days per 28-day cycle.

7. The method of claim 1, wherein the administering steps (i) and (ii) are performed on consecutive days per 28-day cycle.

8. The method of claim 1, wherein the administering steps (i) and (ii) are performed on non-consecutive days per 28-day cycle.

9. The method of claim 1, wherein the CDA substrate drug is decitabine.

10. The method of claim 1, wherein the CDA substrate drug is 5-azacytidine.

11. The method of claim 9, wherein the effective amount of decitabine is from about 15 mg to about 75 mg cumulative per 28-day cycle of treatment.

12. The method of claim 10, wherein the effective amount of 5-azacytidine is from about 10 mg per dose to about 450 mg per dose.

13. The method of claim 10, wherein the effective amount of 5-azacytidine is from about 10 mg to about 3500 mg cumulative per 28-day cycle of treatment.

14. The method of claim 1, wherein the effective amount of cedazuridine is from about 40 mg per dose to about 1000 mg per dose.

15. The method of claim 14, wherein the effective amount of cedazuridine is about 100 mg per dose.

16. The method of claim 1, wherein the effective amount of cedazuridine is from about 100 mg to about 7000 mg cumulative per 28-day cycle of treatment.

17. The method of claim 1, wherein the CDA substrate drug and cedazuridine are administered intravenously, orally, or subcutaneously.

18. The method of claim 1, wherein the subject is a mammal.

19. The method of claim 18, wherein the subject is a human.

\* \* \* \* \*

UNITED STATES PATENT AND TRADEMARK OFFICE
CERTIFICATE OF CORRECTION

PATENT NO. : 11,660,310 B2
APPLICATION NO. : 17/560485
DATED : May 30, 2023
INVENTOR(S) : Keer et al.

Page 1 of 1

It is certified that error appears in the above-identified patent and that said Letters Patent is hereby corrected as shown below:

On the Title Page (56) References cited, OTHER PUBLICATIONS, Column 1, Cite "Steensma, D.": Please correct "18:817-818" to read --18:S17-S18--

(56) References cited, OTHER PUBLICATIONS, Column 2, Cite Desimone, et al.: Please correct "On otarget" to read --Oncotarget--

(56) References cited, OTHER PUBLICATIONS, Column 2, Cite Lemaire, et al.: Please correct "aza-'-deoxycytidine" to read --5-aza-2'-deoxycytidine--

In the Specification

Column 10, Line 6: Please correct "(e.g., e.g.," to read --(e.g.,--

Column 11, Line 45: Please correct "8, 8, 9" to read --8, 9,--

Column 19, TABLE 1: Please delete TABLE 1 and replace with the following:

| Cohort (n=6 each) | Decitabine Dose (mg) | Cedazuridine Dose (mg) | Schedule (28-Day Cycle) | Total Cedazuridine Dose (mg/cycle) | Total Decitabine Dose (mg/cycle) |
|---|---|---|---|---|---|
| 1 | 5 | 100 | Daily×5, Off ×2, Daily×5 | 1000 | 50 |
| 2 | 10 | | | | 100 |
| 3 | 15 | | | | 150 |

Signed and Sealed this
First Day of August, 2023

Katherine Kelly Vidal
*Director of the United States Patent and Trademark Office*